United States Patent
Busuttil

(10) Patent No.: US 7,033,332 B2
(45) Date of Patent: Apr. 25, 2006

(54) WRIST SUPPORT BRACE FOR ALLEVIATING CONTRACTURES

(76) Inventor: Robert Busuttil, 367 Ervilla St., Suite A, Pomona, CA (US) 91767-3022

( * ) Notice: Subject to any disclaimer, the term of this patent is extended or adjusted under 35 U.S.C. 154(b) by 0 days.

(21) Appl. No.: 10/887,161

(22) Filed: Jul. 8, 2004

(65) Prior Publication Data

US 2006/0009724 A1    Jan. 12, 2006

(51) Int. Cl.
*A61F 13/00*    (2006.01)
(52) U.S. Cl. ............... 602/21; 602/5; 602/62; 602/64
(58) Field of Classification Search ........... 602/5, 602/21, 62, 64; 128/878, 879; 482/105, 482/44
See application file for complete search history.

(56) References Cited

U.S. PATENT DOCUMENTS

| 2,692,594 | A | * | 10/1954 | Kelly | 602/21 |
| 2,767,708 | A | * | 10/1956 | Keropian | 602/21 |
| 3,814,419 | A | * | 6/1974 | Bjorklund et al. | 482/124 |
| 4,361,142 | A | * | 11/1982 | Lewis et al. | 602/16 |
| 4,456,002 | A | * | 6/1984 | Barber et al. | 602/22 |
| 4,657,000 | A | * | 4/1987 | Hepburn | 602/16 |
| 4,665,905 | A | * | 5/1987 | Brown | 602/16 |
| 4,677,971 | A | * | 7/1987 | Lindemann | 602/21 |
| 4,790,300 | A | | 12/1988 | Marx | |
| 4,977,890 | A | | 12/1990 | Mann | |
| 5,038,764 | A | * | 8/1991 | Paez | 602/22 |
| 5,205,812 | A | | 4/1993 | Wasserman | |
| 5,437,620 | A | | 8/1995 | Shelly | |
| 5,520,625 | A | | 5/1996 | Malewicz | |
| 5,601,597 | A | | 2/1997 | Arrowood et al. | |
| 5,772,620 | A | | 6/1998 | Szlema et al. | |
| 5,916,186 | A | * | 6/1999 | Turto et al. | 602/20 |
| 6,001,049 | A | * | 12/1999 | Frey | 482/105 |
| 6,106,492 | A | | 8/2000 | Darcy | |
| 6,120,471 | A | * | 9/2000 | Varn | 602/21 |
| 6,213,921 | B1 | * | 4/2001 | Frey | 482/105 |
| 6,456,884 | B1 | * | 9/2002 | Kenney | 607/48 |
| 2002/0035342 | A1 | | 3/2002 | Williams | |
| 2002/0072696 | A1 | | 6/2002 | Varn | |
| 2002/0082538 | A1 | | 6/2002 | Holland et al. | |
| 2003/0078531 | A1 | | 4/2003 | Mhuyen | |
| 2005/0075594 | A1 | * | 4/2005 | Hepburn et al. | 602/16 |

* cited by examiner

*Primary Examiner*—Henry Bennett
*Assistant Examiner*—Dinnatia Doster-Greene
(74) *Attorney, Agent, or Firm*—Brande and McCleary; Lewis M. Brande; Thomas A. McCleary

(57) ABSTRACT

A wrist support brace for patients with contractured wrists utilizes an adjustable strap to physically force the contractured wrist into a non-contractured position, thereby allowing the wrist to heal in a normal position.

3 Claims, 3 Drawing Sheets

WRIST SUPPORT BRACE FOR ALLEVIATING CONTRACTURES

1. BACKGROUND OF THE INVENTION

Figure 1:
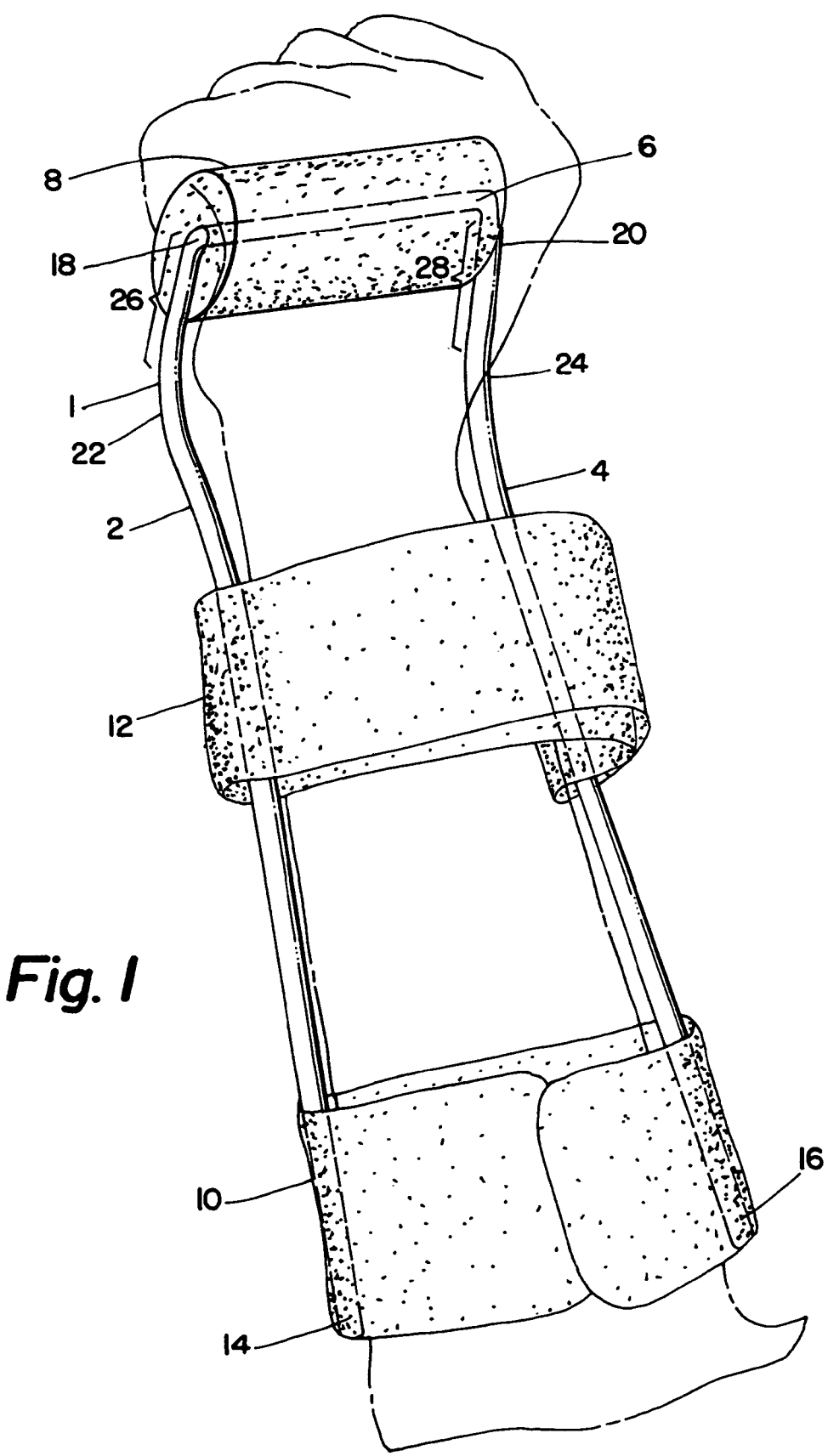
Figure 2:
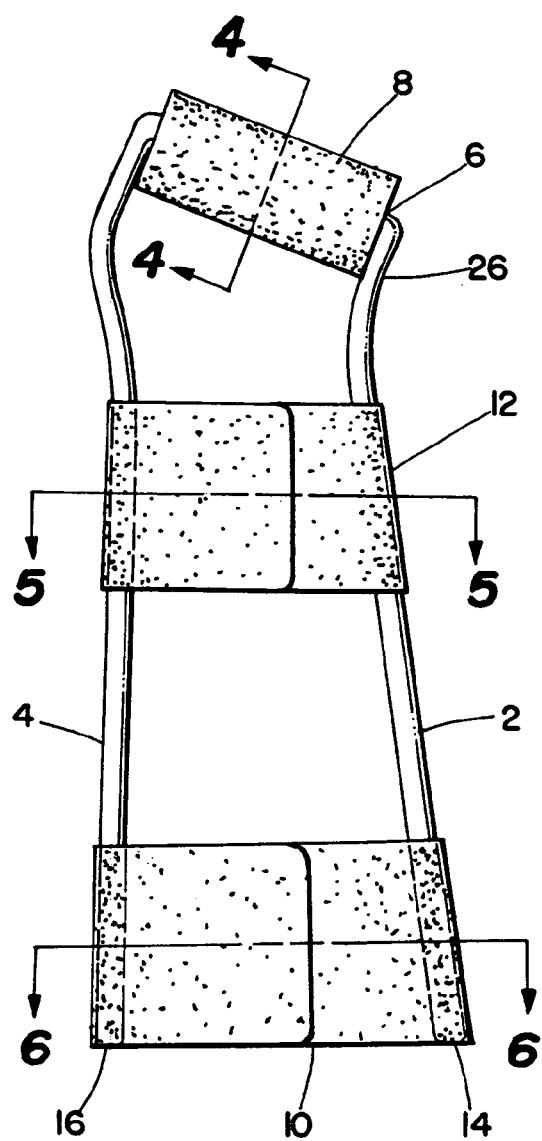
Figure 3:
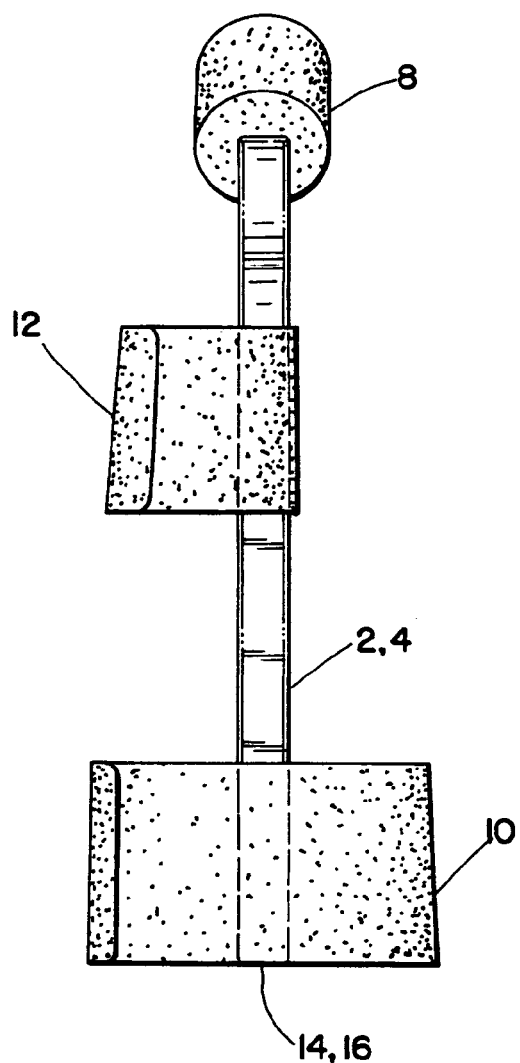
Figure 4:
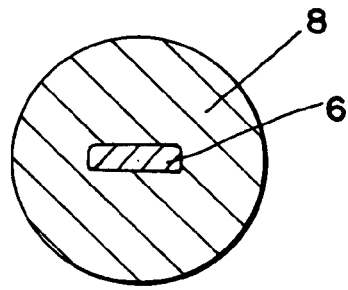
Figure 5:
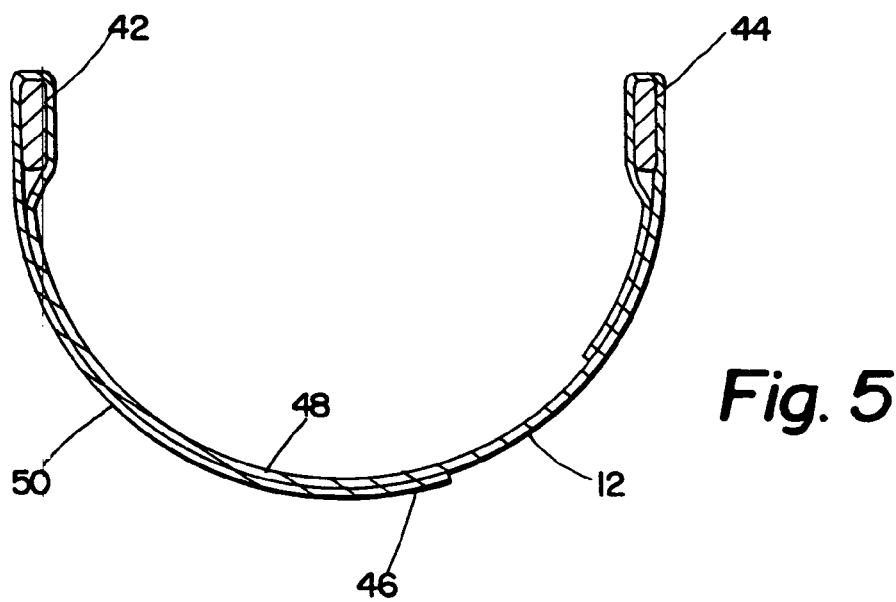
Figure 6:
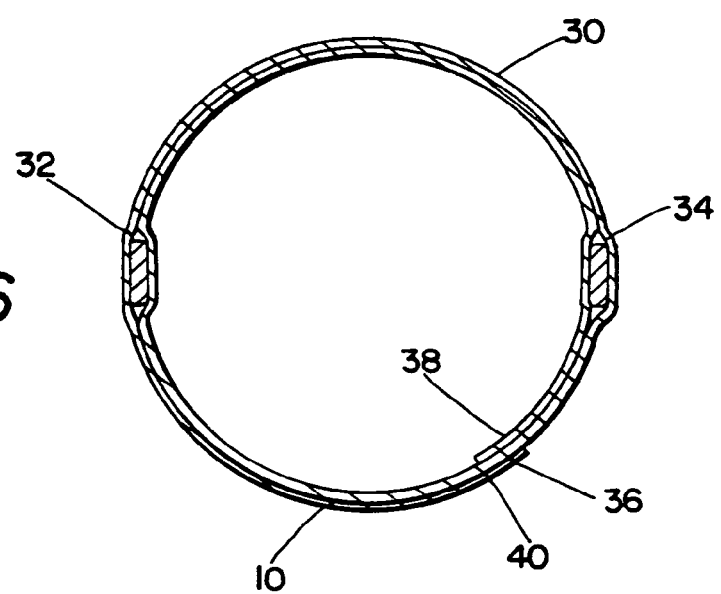

This invention relates to the field of wrist supports. More specifically the invention relates to an device in the field of orthotics. The device is used to assist a person who suffers from forms of strokes, paralysis, or other forms of musculature or nerve disease or damage that require manual straightening of the wrist to restore the appendage to normal everyday use.

2. DESCRIPTION OF THE PRIOR ART

Various types of braces and appliances for therapeutic use in treating bone or muscle disorders are described in the prior art. Several patents exist to assist patients in restoring a hand that is contracted to normal condition.

A typical device is described by U.S. Pat. No. 5,437,620 by Shelly which discloses a "Wrist Splint". This device bladders that assist in supporting the hand. The wrist is supported by rigid non-pliable platform. Straps are used that wrap around the platform and over the wrist applying pressure to straighten the wrist during the contractions.

Another device is U.S. Pat. No. 5,601,597 by Arrowood et al., which discloses "Combination Radial Artery Occluder and Wrist Splint". This device is specifically used to immobilize a wrist in order to prevent further damage or injury to an artery. The device is made specifically to prevent flow through the radial artery by applying pressure and allowing blood flow through the ulnar artery. Although the device does comprise a rigid member, the rigid member is not specifically needed to straighten the wrist, but only to maintain the wrist in an immobile state.

U.S. Pat. No. 5,772,620 by Szlema et al. discloses a "Hand and Wrist Joint Orthosis". This device was created to immobilize an injured hand. The wrist and the fingers are maintained in a specific orientation to each other to guarantee good recovery from an injury. The device is not designed to be used for wrist contractures, in where the wrist must be forcibly dislocated.

U.S. Pat. No. 6,106,492, publication number U.S. 2002/0035342 A1, and U.S. 2002/0072696 A1 are inventions that are specifically related to treatment of carpal tunnel injuries. These devices immobilize the wrist and are designed to prevent unwanted movement of the wrist, which will cause further injury to the carpal nerve system in the wrist. The devices are distinguished from the present invention in that they are not designed to apply the force necessary to forcibly straighten the wrist that has been stricken with a contracture.

Patent Publication Number U.S. 2002/0082538 A1 discloses an "Orthotic Device for Treating Contractures of Either Hand". This device uses a soft padded envelope or mitt that is mated with a splint. The device has padded attachment straps that are located at different regions of the mitt. This device uses a mitt, which is made from a manually bendable material such as metal encased in a soft plastic padding. It should be noted that there is a great difference to the present invention in that the present invention is not made from bendable flat sheet metal, which is needed for Patent Publication Number U.S. 2002/0082538 A1 to be built. Additionally the method by which the straps are used is different from the present invention, in that the straps to Patent Publication Number U.S. 2002/0082538 A1 wrap over the wrist making it very difficult for a sole person, without assistance, to apply enough pulling force onto the straps to cause the constricted appendage to be forcibly straightened.

3. SUMMARY OF THE INVENTION.

In accordance with the present invention, there is provided a new and novel orthotic device that has been designed to assist a person in alleviating contractures of a person's wrist. This particular device may be used for either the left or right hand. This device has been made by bending a metallic bar that may be made from metals such as aluminum, titanium, or steel. The metal is stiff enough to prevent a user from bending the device out of shape. The device comprises two essentially parallel bars, one on each side of the arm that extend towards the arm. The two bars follow a $90^{th}$ percentile persons wrist/hand shape and are joined at the hand. The general shape would be considered a deep "C" shape, where the two bars are joined by a elongated hand support region. Foam is wrapped around the hand area to provide the user with a easily gripped surface. At least two velcro straps are included with the orthotic device, and wrap around the wrist and the forearm.

It is the object of the present invention to provide an orthotic device that can treat contractures of the wrist or hand.

It is a further object of the invention to provide an orthotic device that would allow a patient to easily apply a force perpendicular to the contracture without the assistance of another person.

A still further object of the invention is to provide an orthotic device that is easily fabricated and may be used on either wrist or hand.

Yet another object of the invention is to provide an orthotic device that has a designed shape that provides the smallest profile form, thus preventing serious interference with a patients normal use of his wrist or hand.

These and other objects, features and advantages of the present invention will be come apparent to those skilled the art from the following detailed description and attached drawings, upon which, by way of example, only a preferred and other important embodiments of the invention are described and illustrated.

4. BRIEF DESCRIPTION OF THE DRAWINGS

1. Figure one (1) shows a perspective view of the wrist support brace with a users arm
2. Figure two (2) shows a plan view of the wrist support brace
3. Figure three (3) shows a side view of the wrist support brace
4. Figure four (4) shows a cross sectional view of the grip pad and grip support
5. Figure five (5) shows a cross sectional view of the adjustable strap
6. Figure six (6) shows a cross sectional view of the forearm strap

5. DETAILED DESCRIPTION

With respect to figure one (1), what is shown is a wrist support brace (1). The wrist support brace (1) is shown having an ulnar support (2), and a radial support (4). The ulnar support (2) and the radial support (4) may be positioned in a parallel relationship, or as shown in figure one (1) in a diverging, non-parallel relationship. A first end (14) of the ulnar support (2), and a first end (16) of the radial support (4) are spaced further apart than a second end (18) of the ulnar support (2) and a second end (20) of the radial support (4). The second end (20) of the radial support (4) and the second end (18) ulnar support (2) are joined by a grip support (6) with a grip pad (8).

With respect to figure two (2), the wrist support brace (1) is shown in plan view. The ulnar support (2) is shown having a ulnar support kick point (22), and the radial support (4) is shown having a radial support kick point (24). The ulnar support (2) is bent about the ulnar support kick point (22), and the radial support (4) is bent about the radial support kick point (24). A first bent portion (26) of the ulnar support (2) and a first bent portion (28) of the radial support (4) are positioned in an approximate parallel relationship, wherein the grip support (6) is shown attached the first bent portion (26) of the ulnar support (2) and the first bent portion (28) of the radial support (4) in nearly a right angle orientation. In order to maximize the utility of the wrist support brace (1), the ulna support (2), the radial support (4), and the wrist support (6) are shown lying in a planar relationship.

For maximum comfort, the first bent portion (26) of the ulnar support (2) and the first bent portion (28) of the radial support (4) are shown having a space between a users closed fist and the first bent portion (26) of the ulnar support (2) and the first bent portion (28) of the radial support (4).

The forearm strap (10) has a first ulnar slot (32) and a first radial slot (34) defined therein. The first ulnar slot (32) allows the ulnar support (2) to pass therethrough, and the first radial slot (34) allows the radial support (4) to pass therethrough. The forearm strap (10) is shown being looped around the ulnar support (2) and the radial support (4) creating a forearm cradle (30). A reusable self adhesive portion (36) typically made from materials similar to Velcro®. The reusable self adhesive portion (36) has a first strap (38) and a second strap (40). The first strap (38) laying on the forearm of a user, the second strap (40) overlapping the first strap (38) and being fastened thereby, fixing the wrist support brace into position.

The adjustable strap (12) is located at the approximate midpoints of the ulnar and radial supports and is comprised of a second radial slot (44), the second radial slot (44) being looped around the radial support
and being positionally fixed. The adjustable strap (12) further has a third strap (48). The third strap
wraps over a users contractured wrist, and under the ulnar support (2), looping around thereby, creating a second ulnar slot (42). The second ulnar slot (42) not being fixed in position, but allowing a user to apply leverage to a contractured wrist, reducing the contracture thereby. A fourth strap (50) is the continuation of the adjustable strap (12). The fourth strap (50), has a second self adhesive portion (46), the second self adhesive portion (46) being constructed from hook and loop materials common within the industry and commonly known as Velcro®. When the user has applied sufficient force to minimize the wrist contracture, the second self adhesive portion (46) will fix the adjustable strap (12) into position, providing wrist support.

In essence, the wrist support brace (1) is operated as follows. A user with a wrist contracture will grip the grip pad (8) with his fist. The user will then wrap the forearm strap (10) around his/her forearm, fixing the wrist support brace (1) in position. At this point the wrist is generally contracted upwards. The adjustable strap (12) is wrapped over the contracted wrist, and under the radial support (4). The user applies as much force as necessary by pulling the adjustable strap (4) forcing the wrist downwards into a non-contractured position. The fourth strap (50), an extension of the adjustable strap (12), is then wrapped over the wrist and adjustable strap (12) where the second self adhesive portion (46) is located. The fourth strap (50) is then attached to the adjustable strap (12) fixing the adjustable strap and thereby immobilizing the contractured wrist to a natural position.

Although the foregoing includes a description of the best mode contemplated for carrying out the invention, various modifications are contemplated.

As various modifications could be made in the constructions herein described and illustrated without departing from the scope of the invention, it is intended that all matter contained in the foregoing description or shown in the accompanying drawings shall be interpreted as illustrative rather than limiting.

What is claimed is:

1. A wrist support brace comprising:
   a. an ulnar support, said ulnar support having a first end and an second end, a radial support, said radial support having a first end and a second end, a grip support, said grip support being attached to said second end of said ulnar support and said second end of said radial support, said ulnar support, said radial support and said grip support being defined in a planar relationship, a grip pad, said grip pad being attached to said grip support;
   b. in addition, said radial support and said ulnar support are defined in a diverging relationship wherein said second ends of said radial and said ulnar supports being spatially closer than said first ends of said ulnar and said radial supports, said second end of said ulnar support having a first bent portion, said first bent portion of said ulnar support being bent about an ulnar support kick point, said second end of said radial support having a first bent portion of said radial support being bent around a radial support kick point said first bent portion of said ulnar support and said first bent portion of said radial support being in an essentially parallel relationship providing clearance to a patient's wrist and fist thereby;
   c. a forearm strap, said forearm strap being attached to a first end of said radial support and having self adhesive attach means defined thereon, said forearm strap being attached to said first end of said ulnar support creating a cradle therebetween, a second strap, said second strap wrapping around a patient's forearm and being removably attached to a first strap; and
   d. an adjustable strap, said adjustable strap having self adhesive attach means attached thereon, said adjustable strap also being attached to said radial support and being positionally fixed at an approximate midpoint of said radial support, said adjustable strap having a third strap, said third strap wrapping over a patient's contractured wrist and under said ulnar support, said adjustable strap having a fourth strap with means to removably attach itself to said adjustable strap wherein a patient with a wrist contracture can grip said grip pad, wrap the forearm strap around the patient's forearm contracting the patient's forearm upward, then said adjustable strap is wrapped over the patient's wrist and the patient pulls said adjustable strap forcing the patient's wrist downward thereby into a non-contractured position.

2. The wrist support brace of claim 1, wherein: said self adhesive attach means of said forearm strap consists of a hook and loop fastener.

3. The wrist support brace of claim 1, wherein: said self adhesive attach means of said adjustable strap attachment means consists of a hook and loop fastener.

* * * * *